United States Patent [19]
Brooker

[11] 3,959,077
[45] May 25, 1976

[54] ENZYME PREPARATION FOR SERUM CARDIAC GLYCOSIDE ASSAY

[75] Inventor: Gary Brooker, Los Angeles, Calif.

[73] Assignee: The University of Southern California, Los Angeles, Calif.

[22] Filed: Aug. 11, 1972

[21] Appl. No.: 279,817

Related U.S. Application Data

[62] Division of Ser. No. 102,719, Dec. 30, 1970, Pat. No. 3,769,414.

[52] U.S. Cl. .................................. 195/63; 195/68; 195/99; 195/103.5 R; 195/103.7
[51] Int. Cl.² .................. G01N 31/14; C07G 7/02
[58] Field of Search .............. 195/103.5, 63, 66, 62, 195/103.7

[56] References Cited
OTHER PUBLICATIONS

Brooker et al., *Setum Digoxin Levels in Toxic and Nontoxic Patients by Enzymatic Isotope Displacement*, Clinical Research, Vol. 18, Apr. 1970 (p. 299).
Bonting et al., *Studies on Sodium–Potassium–Activated Adenosinetriphosphatase*, Archives of Biochemistry and Biophysics Vol. 98, 1962 (pp. 413–419).
Skoll, J. C., *The Influence of Some Cations on an Adenosine Triphosphatase from Peripheral Nerves*, Biochimica et Biophysica Acta, Vol. 23, 1957 (pp. 394–401).
Dixon, et al., *Enzymes*, 2nd Ed., Academic Press Inc., N.Y., 1964 (pp. 148–150 & 423).

*Primary Examiner*—David M. Naff
*Attorney, Agent, or Firm*—Harris, Kern, Wallen & Tinsley

[57] ABSTRACT

A method of assaying serum cardiac glycoside concentrations employing the principle of enzymatic isotope displacement from an enzymatically produced binding enzyme, a serum extract, and a labeled or isotopic cardiac glycoside. The serum extract is prepared by extracting the serum with a halogenated alkane, and partitioning the extract between a buffered solution and an aromatic hydrocarbon having a molecular weight greater than 80. The binding enzyme is made from an enzymatic preparation of whole brain by reacting the preparation with calcium, sodium, magnesium, and ATP.

13 Claims, 5 Drawing Figures

ENZYME PREPARATION FOR SERUM CARDIAC GLYCOSIDE ASSAY

This is a division of application Ser. No. 102,719, filed Dec. 30, 1970, now U.S. Pat. No. 3,769,414.

The present invention is directed to a serum assay for cardiotonic steroids and their glycosides, hereinafter referred to as cardiac glycosides. Hereafter unless otherwise noted the word "serum" is used to refer to any biological fluid or extract of tissue. Over six million people in the United States are on cardiac glycoside therapy regimens. The principal cardiac glycosides are digoxin, digitoxin, ouabain, lanatoside C, and digitalis leaf, which is a complex mixture of cardiac glycosides. Current knowledge about the mechanism of action of cardiac glycosides suggest that they inhibit the Na-K-ATPase which is found in cell membranes and is thought to play a part in the movement or transport of sodium and potassium, and possibly calcium, across cell membranes. Inhibition of this enzyme by cardiac glycosides results in the cell ending up with more intracellular sodium and calcium in certain components than is normally found. The regional increase in calcium is believed to be responsible for the inotropic action exhibited by the heart tissue when the patient is on cardiac glycoside therapy; that is, the heart beats with greater force and each beat is completed in a shorter time period.

Cardiac glycosides are potent compounds that can readily kill or seriously disable a patient if allowed to build up to high concentrations in the body fluids due to renal malfunction. Most cardiac patients should be placed on digoxin dosage regimens to provide a serum concentration of the glycoside of 2 nanograms or less per ml. of blood; although patients being administered digitalis leaf, digitoxin or gitaligin are maintained on higher serum concentrations. Digoxin, when present at serum concentrations higher than 2 nanograms per ml. increases the risk of arrhythmias appreciably as shown by the following table:

| Concentration in Nanograms per ml. of Blood Serum | Risk of Arrhythmias |
|---|---|
| 1.4 | about 10% |
| 2 | about 25% |
| 2.9 | about 50% |
| 4 | about 66% |
| 5 | about 80% |

Uncontrolled arrhythmia can easily lead to a patient's death and the over-all death rate for arrhythmic patients on cardiac glycoside therapy is about 10%. From recent studies with the present assay it has become evident that 25% of the patients receiving cardiac glycosides had inadvertently been given dosage regimens that led to digitalis toxicity and high serum levels, that is, 25% of the patients are on dosage regimens that give them adverse reactions. Accordingly it is important that a physician have an assay that will provide him with a means of quickly and accurately determining the serum cardiac glycoside concentration in his patient.

Reported therapeutic serum levels of digitalis leaf and digitoxin are about 10 to 20 times higher than those of digoxin. Work with the present assay supports this, with levels of 4 to about 200 Ng/ml being found for the patients studied to date who received these drugs.

To date, six sera have been assayed for digoxin in which results of over 15 Ng/ml of apparent digoxin were obtained. In the absence of digitalis toxicity, such very high levels strongly suggested that the patient might actually be receiving digitalis leaf or digitoxin. A check with the patient's physician revealed that no evidence of digitalis toxicity was present. Further checking by the physician then disclosed that all six patients actually had been receiving either digitalis leaf or digitoxin just prior to admission.

One patient subsequently found to be receiving digitoxin was further studied using a disposable silica gel column chromatography step which effectively separates digitoxin, digoxin, and ouabain from each other prior to assay. It was found that only the digitoxin fraction contained assayable cardiac glycoside.

It is probable that if these sera had been studied by the immunoassay described below, because of the nature of that method, results in the range of 1.5 Ng/ml of apparent digoxin or less, a normal or low digoxin level would have been found thus tending to preserve the false impression that the patients were receiving digoxin perhaps with inadequate dosage. In contrast, the present assay obtained results consistent with reported levels of digitalis leaf and digitoxin, and thus prompted further inquiry which then disclosed the true situation, and it also confirmed it. Without such results, it is probable that the above patients would have been unwittingly subjected to an unknowing replacement of common maintenance doses of digitalis leaf or digitoxin with common doses of digoxin. The results of such an unwitting replacement of a long-acting glycoside by a shorter acting one, with its attendant hazards of digitalis toxicity, have been described.

At the present, besides the novel assay of the present invention there are only three principal methods of measuring serum cardiac glycoside levels in animal serum, none of which are in widespread use because of their complexity and expense.

The digoxin immunoassay of Smith, Butler and Haber takes an animal blood sample and incubates it with a standard amount of radioactive glycoside and its relatively specific antibody. The unbound glycoside, both radioactive and not, is separated. The antibody containing bound radioactive glycoside is counted by liquid scintillation. Appropriate reference standards of nonradioactive glycosides are also prepared in human serum from people not receiving digitalis. This immunoassay has varying specificity to different cardiac glycosides, and it responds most well only to the single cardiac glycoside against which the antibody was originally prepared. Further, it has not been applied to samples outside of human serum itself, such as urine, gastric juice, or tissue samples. In addition, besides its limited application other radiactive materials which may be present in the blood of patients receiving diagnostic or therapeutic radioisotope studies may so contaminate the serum sample for the immunoassay so as to cause serious errors with that assay. Lastly, specificity of the antibody may vary from lot to lot.

The rubidium-86 assay of Lowenstein and Corrill and its various modified forms measures the digitalis-induced inhibition of potassium uptake and turnover in red blood cells, by measuring the inhibition of rubidium-86 uptake, because rubidium is handled by red blood cells similar to potassium. The method employs extraction of serum or plasma with a halogenated alkane, incubation of the extract with standardized red blood cells, separation of the incubated red blood cells and subsequent examination of their ability to take up rubidium-86. The method is laborious, takes much time and is relatively insensitive.

The serum digitoxin assay of Burnette and Conklin measures the inhibition of Na-K-ATPase activity of digitoxin rather than measuring the binding of cardiac glycosides to the enzyme. It employs extraction of glycosides from serum or plasma with an organic solvent, incubation with ATP and a preparation of Na-K-ATPase which is not novel, and spectrophotometric measurement of the digitalis-induced inhibition of inorganic phosphate release as ATP is consumed by that enzyme preparation. The method requires large amounts of blood and still is not sensitive enough to measure the low digoxin levels present in therapeutic amounts in patient serum. It is also time consuming and is probably less specific than the present assay, as inhibition of phosphate release may be caused by materials other than cardiac glycosides such as diuretics.

In the immunoassay of serum digoxin by Smith, Butler and Haber much time is required to prepare the proper antibody. In contrast, the present assay requires only one working day to prepare enzyme precursor for about 1000 assays. This enzyme is highly specific for digitalis compounds in current use, is simple to make, and is stable at −20°C. for at least 3 months. In addition, the assay is easily and rapidly performed each day.

The immunoassay appears to have a 10-fold specificity for digoxin over digitoxin. Because the antibody response is variable from one animal to the next, the specificity of this antibody may also be variable from lot to lot. In contrast, the present assay appears specific for digitalis compounds as a group.

The present assay also appears both more sensitive and precise than various modifications of the red blood cell-rubidium assay first described by Lowenstein and Corrill, *Circulation*, 31:228–233(1965).

In terms of results, the present assay has obtained findings in close general agreement both with the immunoassay and with most of the red blood cell-rubidium-86 assays for serum digoxin. The results for serum digitoxin also show general agreement with both the double isotope dilution derivative assay of plasma digitoxin of Lukas and Peterson, *J. Clin. Invest.*, 45:782–795 (1966), with the plasma digitoxin assay described by Burnett and Conklin, *J. Lab. and Clin. Med.*, 71:1040–1044 (1968), and with the immunoassay of serum digitoxin, Oliver, G. D. et al, *J. Clin. Invest.*, 47:1035–1042 (1968).

SUMMARY OF THE INVENTION

The assay of the present invention is an enzymatic isotope displacement assay from a binding enzyme similar in principle to the displacement assay described in two articles: *Biochemistry*, 7:4177 (1968) and Ibid, 7:4182 (1968). The assay comprises preparing a serum extract of the animal serum which contains a substantial portion of the active cardiac glycosides found in the serum and which is substantially free of components which will interfere with the enzymatic isotope displacement step of the assay. The serum extract is incubated with the novel binding enzyme of the present invention, a radioactive isotope labeled active cardiac glycoside, and certain components necessary for the successful displacement reaction. After incubation, the mixture is centrifuged down and the radioactive isotope concentration of the supernatant is counted in a liquid scintillation counter; this count is proportional to the active cardiac glycoside concentration in the animal serum. The novel binding enzyme of the present invention is prepared from a binding enzyme precursor by reacting the latter with sodium, magnesium, and ATP. The precursor is prepared from an enzymatic preparation, which is isolated from whole animal brain by reacting the latter with calcium.

An object of the present invention is to provide a simple and inexpensive method of assaying active cardiac glycoside concentrations in animal serums. More particularly, it is an object to provide an assay that is accurate, requires less than 2 milliliters of the animal serum, and can be quickly done, and can be used clinically in all community hospitals.

Figure 1:
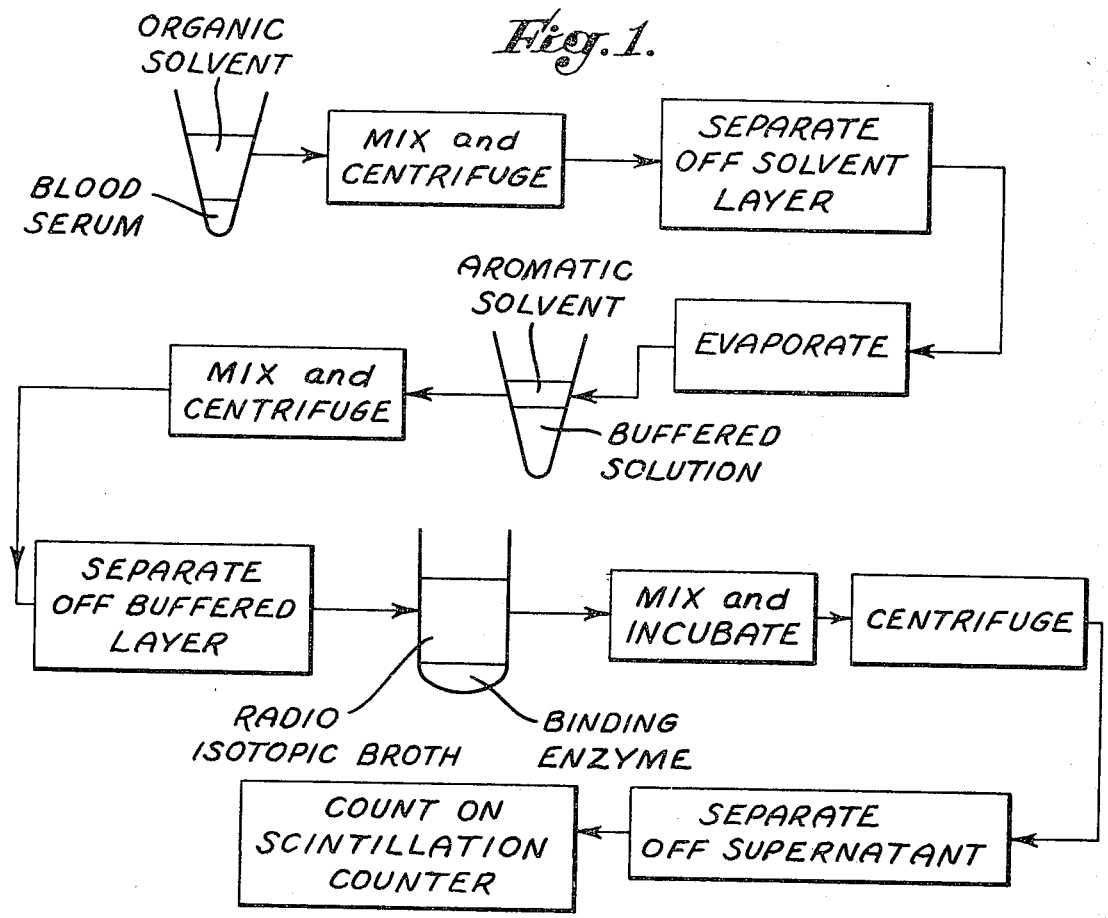
FIG. 1 is a schematic diagram of the assay of the present invention.

The assay of the present invention comprises several steps as schematically shown in FIG. 1. The animal serum to be assayed is first mixed with a water immiscible organic solvent. The solvent of choice is a halogenated alkane having a molecular weight of less than 200 and boiling at less than 100° C. Typical halogenated alkanes that can be employed in the present invention include chloroform, methylene chloride, trichlorofluoro methane, dichloroethane, dichlorofluoroethane, and dichlorodifluoroethane and the like. At least equal volumes of the organic solvent are mixed with each volume of the animal serum; preferably, four or five volumes of the organic solvent are employed for each volume of the serum. This solvent serum mixture is thoroughly mixed and then the organic solvent and serum layers are separated. Generally, the separation is carried out by conventional means such as by centrifuging the mixture. The two layers are separated from each other and the serum layer is discarded. The organic solvent layer is evaporated to dryness. The evaporation can be carried out with heat, a stream of dry air, or under vacuum. The residue remaining after the solvent is evaporated off is taken up with an aqueous buffered solution and mixed with an aromatic solvent. The buffering agent employed in the buffered solution can be any of the buffering agents normally employed in enzymatic preparations. Typical buffering agents that can be employed in the present invention include tris-HCl (the hydrochloride salt of tris (hydroxymethyl) aminomethane, tris-$SO_4$, sodium carbonate, sodium barbital, Good's buffers [Good, N. E. et al, Biochemistry, 5:467–477 (1966)] and the like. The buffered solution has molarity sufficient to maintain the solutions at a stable pH. I have found that a buffered solution having a molarity of 100 millimoles per liter of tris-HCl is a suitable buffered solution for purposes of the present invention. The pH of the buffered solution is preferably maintained between about 6 and about 9, preferably at about 8. It is important that the selected pH does not change during the reaction. The aromatic solvents are those aromatic solvents that are immiscible with water including toluene and xylene. I have found that benzene does not work satisfactorily in this assay because as its relatively high solubility in water inactivates the enzyme or its precursor. The solvent-buffered solution mixture is thoroughly mixed and the fractions are thereafter separated by conventional methods, such as by centrifuging. The relative volumes of the aromatic solvent and the buffered solution are selected to provide that a substantial portion of the cardiac glycosides remain in the aqueous phase, and a substantial portion of the interfering components go into the organic phase. I have found that 20 volumes of toluene to 130 volumes of aqueous and 100 millimolar tris-HCl makes a satisfactory volume ratio. After separation, the aromatic solvent layer or fraction is discarded leaving the serum extract, that is, the buffered solution fraction. In the above procedure a substantial portion of the cardiac glycosides in the animal serum are concentrated in the serum extract. The serum extract is substantially free of interfering components present in the animal serum. By "interfering components," I mean those components found in the animal serum that interfere with the radioisotope displacement from the binding enzyme in the following step.

The serum extract and aqueous buffered mixtures having known concentrations of cardiac glycosides (hereinafter referred to as standard samples) are incubated with aqueous buffered mixtures containing the novel binding enzyme of the present invention in the presence of radioactive isotope cardiac glycoside, magnesium and sodium ions, ATP a buffering agent and optionally, but preferably, a heavy metal chelating agent. It is preferably that potassium be eliminated from the reagents to optimize the sensitivity of the assay. Ten microliters of the extract are sufficient for the incubation, although smaller and larger amounts may be employed. The binding enzyme is prepared by reacting a binding enzyme precursor or binding material (described below) with a high energy phosphate compound such as adenosine triphosphate (ATP), adenosine diphosphate (ADP), guanosine triphosphate (GTP), guanosine diphosphate (GDP) and the like. The reaction is preferably conducted in the presence of magnesium and/or sodium, preferably both. The reaction is conveniently carried out in the incubation or displacement step reaction mixture. About 4 to 100 micromoles of the high energy phosphate compound are reacted with each amount of the binding enzyme precursor prepared from one gram of animal tissue; although lesser or greater amounts of a high energy phosphate compound may be used. The important thing is to react the precursor with a sufficient amount of the high energy phosphate compound to obtain enough of the binding enzyme for the displacement assay. The binding enzyme appears to have a relatively short half-life, whereas the binding enzyme precursor and binding material have a relatively long half-life. Thus I have found it convenient to prepare fresh enzyme for each assay from stored precursor or material. Moreover, because of the relatively short half-life of the enzyme, it is advantageous to incubate all the components together, preferably simultaneously. For the amount of serum extract prepared from one ml. of animal serum, about 10 $\mu$ (microliters) are used in the assay; however, lesser or greater amounts may be used. The term one "equivalent of serum extract" for purposes of this invention means the amount of extract prepared from one ml. of animal serum. Sufficient amounts of binding enzyme are employed to obtain substantial binding of the radioisotope labeled cardiac glycoside in the absence of unlabeled glycoside.

For the amount of serum extracted prepared from one milliliter of animal serum, between about 5 to 5000 nanomoles of magnesium, between about 0.1 to 60 micromoles of sodium and, optionally, between about 5 to 5000 nanomoles of a heavy metal chelating agent are employed. It is also satisfactory to employ between about 2 and 2000 micromoles of magnesium, between about 2 and 2000 micromoles of EGTA, between about 10 and 250 millimoles of ATP, and between about 0.04 and 24 millimoles of sodium. A sufficient amount of the radioactive isotope labeled glycoside is employed so that the unlabeled glycoside concentration can be determined by the displacement reaction. For the amount of serum extract prepared from one milliliter of serum, a labeled glycoside concentration of at least 0.1 nanocurie; preferably at least 0.04 $\mu$Ci is used. A sufficient amount of buffering agent is used to insure that the incubation mixture will maintain a relatively constant pH between about 6 and 9. The pH of the incubation mixture is adjusted to a value between 6 and 9, preferably at the pK of the buffer.

I have found that the concentrations of the components in the displacement reaction are relatively important. Concentrations of about 0.1 to 50 mM (millimolar) of magnesium ion; of about 0.1 to 50 mM of the high energy phosphate compound; of about 0.1 to 50 mM of the heavy metal chelating agent; and of about 1 to 600 mM of sodium are satisfactory for the displacement reaction. The preferred concentrations are 5 mM of the high energy phosphate compound, 5 mM of magnesium, 5 mM of the heavy metal chelating agent and 100 mM of sodium. The extract concentration is rarely less than 5 $\mu$ per millimeter of serum, preferably 25 $\mu$ or greater depending upon the amount of cardiac glycoside present.

By the term "heavy metal chelating agents" is meant those chelating agents that preferentially chelate with heavy metals having an atomic weight greater than 25, such as calcium, manganese, copper and the like. A preferred heavy metal chelating agent is ethylene bis (oxyethylene-nitrilo) tetraacetic acid (EGTA).

I have found tritiated ouabain to be a suitable radioactive isotope labeled cardiac glycoside for the displacement step, although other active cardiac glycosides and radioactive isotopes can be employed. For example, digoxin would be a suitable glycoside and iodine 131 would be a suitable isotope. For example, the iodine could be attached to the aglycone of glycoside by esterifying the 3-hydroxy on the aglycone or other hydroxy groups on the glycoside with iodoacetyl chloride and then heating the iodoacetate ester in aqueous HI containing sodium iodide 131 wherein iodine 131 exchanges with the iodine on the acetyl group. As shown and explained in the article *Biochemistry* 7:4182 (1968) the sensitivity of an enzymatic binding radioisotope displacement assay increases with the employment of a more highly radioactive labeled compound. For example, the use of $H^3$ ouabain having a specific activity of 22.6 Ci/millimole in the present assay would increase the assay's sensitivity two-fold with respect to the amount of animal serum needed for the assay. Theoretically, the specific activity could be raised to a value, such as 5000 Ci/millimole, wherein only one microliter of animal serum would be required to run an assay. This would be a benefit to both clinical and forensic medicine.

Figure 2:
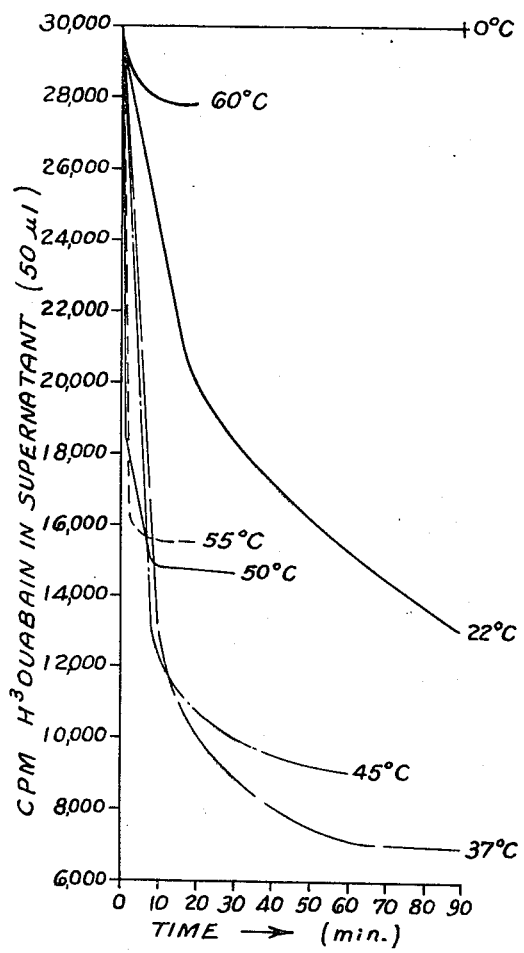
FIG. 2 is a graph showing the reaction rate for production of the isotope binding enzyme step of the present invention with respect to reaction temperature.

Each of the aqueous mixtures is incubated between a temperature of 1°C. and 60°C., preferably at a temperature between about 25°C. and 55°C. During the incubation, the glycoside being assayed and the labeled glycoside compete in binding with the binding enzyme. The reaction or binding rate is temperature dependent as shown in FIG. 2. At an incubation temperature of 37°C., the binding reaction reaches equilibrium in about 1 hour; whereas at a temperature of 55°C., equilibrium is reached in about 10 minutes. At temperatures above 60°C., the binding enzyme is denatured or inactivated and little if any binding occurs.

After the incubation period, each mixture is separated by conventional methods, such as by centrifuging down to separate a clear supernatant that contains unbound radioactive isotope labeled glycoside. An advantage of this assay is that a low centrifugation force, such as a force of 500 × g or less, is sufficient to separate the bound from the unbound cardiac glycosides. I have found that an ordinary bench top clincal centrifuge is sufficient for this separation. Each mixture's supernatant is separated from the solid and its radioactivity concentration is counted on a scintillation counter. The glycoside concentration of the animal serum is readily determined by comparing the supernatant count with the counts from the various standard samples. When standard incubation mixtures are employed, a standard chart, such as FIG. 3, can be prepared which will readily provide a means of determining the glycoside concentration for an animal serum assay. For example, a count of 7000 CPM in an assay would indicate (FIG. 3) that a 1 ml. animal serum sample contained about 3.6 nanograms of digoxin, a toxic concentration.

Figure 4:
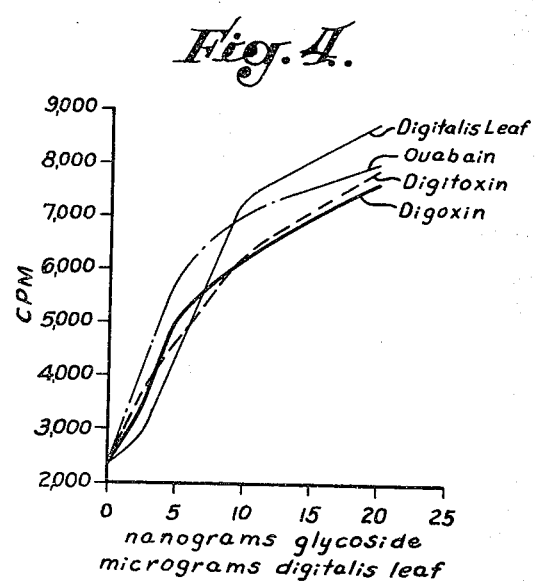
FIG. 4 is a graph plotting various active cardiac glycoside concentrations v. counts per minute of isotope displaced from the binding enzyme to the supernatant after reaction in the displacement step.
Figure 5:
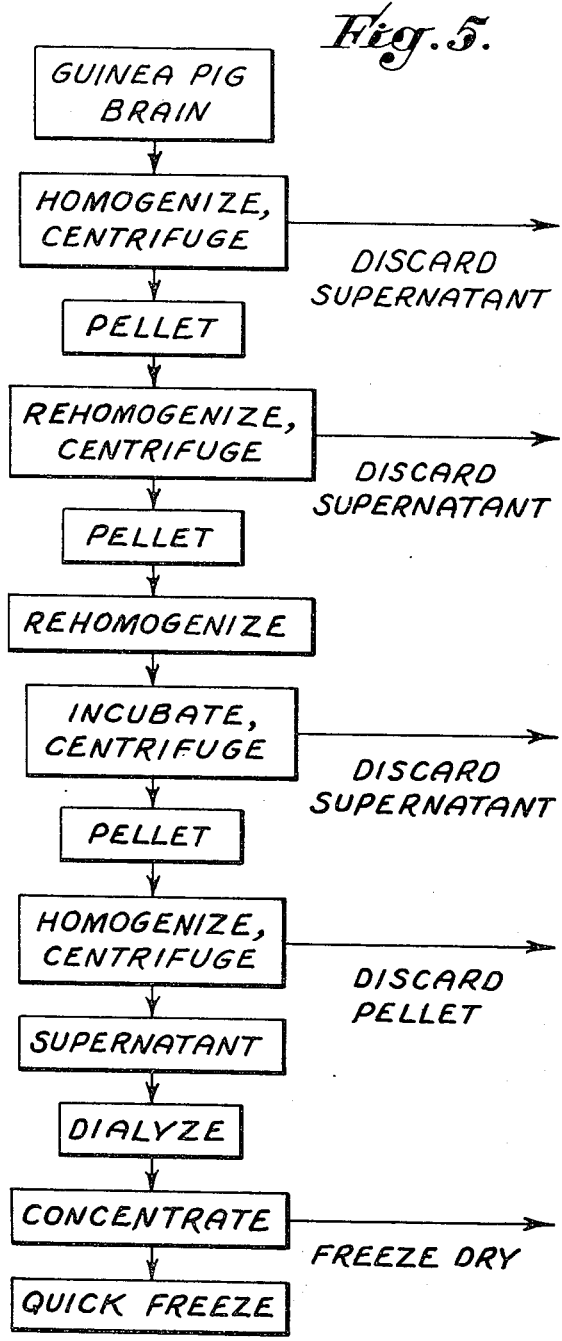
FIG. 5 is a schematic diagram of the process for preparing the novel binding enzyme precursor of the present invention.

As shown in FIG. 4, the more common active cardiac glycosides give relatively similar results. However, in the preferred embodiment of the assay, standards are run with each assay or standard curves are prepared for each cardiac glycoside. Preferably, standard samples are run with each assay when determining the serum concentration of digitalis leaf because digitalis leaf is a complex mixture of glycosides and the composition of digitalis leaf may vary from lot to lot.

The animal serum can be any of the body fluids, such as blood, blood plasma, blood serum, gastric juices, urine or lymphatic fluid. It can also be an extract of tissue. Most commonly, however, the assay will be run on whole blood, blood plasma, blood serum, or urine. The present assay can be used to standardize pharmaceutical preparations of digitalis leaf or other cardiac glycosides.

The surprising accuracy of this assay is believed to be due in great part to two features of the assay: (1) the serum extract preparation and (2) the enzymatic binding radioactive isotopic displacement step. The serum extract procedure requires between 5 and 20 minutes, yet it provides an extract containing a substantial portion of the serum's cardiac glycosides (about 90% when the glycoside is digoxin) and being substantially free of serum components that interfere with the enzymatic binding displacement step. The displacement step is believed to parallel the interaction of active cardiac glycosides and Na-K-ATPase in cell membranes. Very few, if any, compounds are known to interact with Na-K-ATPase beside active cardiac glycosides. Accordingly, I believe the use of a binding enzyme exhibiting Na-K-ATPase activity in the assay minimizes the chance that other components will interfere with the assay.

Alternatively, other labeled cardiac glycosides can be employed in the present assay in lieu of radioisotopic labeled glycosides. For example, the glycoside can be labeled with a group which will enable an operator to determine the concentration of the bound or unbound labeled glycoside in the displacement reaction by photometric means. Typical groups would include fluorescent groups and photo-absorptive groups.

The novel binding enzyme precursor of the present invention is made from animal tissue, preferably from tissue of an animal sensitive to cardiac glycosides, such as guinea pig, monkey, beef, and rabbit, and from tissue having Na-KATPase activity, such as brain, muscle, heart, nerve or kidney. For purposes of this invention the term "one equivalent of binding enzyme precursor or binding material" means that amount of enzyme precursor or binding material prepared from one gram of animal tissue. The binding enzyme precursor is prepared by gently homogenizing the whole tissue in an inert aqueous osmotic solution, such as a sugar solution. The homogenizing is done rapidly within a minute or so at low temperatures between freezing and about 10°C. The osmotic solution is preferably a sugar solution of between about 0.1 and 0.5 molarity. The homogenate is separated by conventional means, such as centrifuging down. When the homogenate is made up of 0.25M sucrose solution, I have found centrifuging the homogenate at about 2600 × g for about 20 minutes adequately separates the homogenate fractions. The liquid phase is discarded and the remaining solid is homogenized in a buffered solution maintained at a pH between about 6 and 9. Any buffering agent that is compatible with the preparation may be employed in the solution, such as those described above. I have found that tris-HCl is a suitable buffering agent in concentrations between about 2 and 10 millimolar. The homogenate fractions are separated by conventional methods, such as centrifuging. When employing a 5mM Tris-HCl buffered solution, I have found the fractions are adequately separated when the homogenate is centrifuged at about 2600 × g for about 20 minutes. The liquid phase is discarded and the homogenate solid is preferably subjected to the above procedure at least two more times, to yield the enzyme precursor preparation.

The enzyme precursor preparation is suspended or mixed in a buffered solution having a pH of between about 6 and 9. The enzyme precursor preparation is reacted with an alkaline earth metal, preferably calcium, at a pH between about 6 and 9, preferably about 7. The alkaline earth metal is present in the aqueous reaction mixture as a soluble salt, such as a soluble calcium salt like calcium chloride or calcium nitrate. Between 0.01 to 0.2 millimole of the alkaline earth metal is used for each gram of whole brain used in the preparation. A concentration of between 1 and 10 millimolar of alkali earth metal is generally used for the reaction. The reaction mixture is gently, but thoroughly, mixed and warmed to a reaction temperature of about 30°C.; although lesser or greater reaction temperatures may be used. At 30°C. the reaction is complete in less than 1 hour. After the reaction, the binding enzyme precursor is cooled to a temperature below 10°C. and separated from the liquid phase by conventional methods, such as by centrifuging. The liquid phase is discarded.

The binding enzyme precursor is purified by mixing the separated solid with an inert osmotic solution, such as a sugar solution having a molarity between about 0.1 and 1. The mixture is separated by conventional means such as being centrifuged for about 5 minutes at about 220 × g (at tip) when the final molarity is about 0.3 or an equivalent centriguation for mixtures of different molarity and for different centrifuging time periods.

By the term "inert osmotic solution" is meant osmotic solutions that will not interact with the binding enzyme precursor or binding material.

The milky supernatant is separated by conventional means such as being decanted from the solid and dialyzed at a temperature between 0°C. and 10°C. against an aqueous buffered hypo-osmotic solution, to remove excess free calcium and other reagents from the prior steps. The dialysis is continued until equilibrium is achieved. The pH of the dialysis solution should be between 6 and 9, preferably about 8. The dialyzed material is then concentrated, preferably to a volume of between about 2 to 10 ml. for each gram of whole tissue used in the preparation. However, centrifugation in a relatively large volume of aqueous buffered hypo-osmotic solution may also be used instead of the dialysis step. The concentrated material is gently homogenized one more time and either frozen at a temperature below freezing or freeze-dried. Optionally the binding enzyme precursor can be freeze-dried after the dialysis step.

When freeze-dried, the binding enzyme precursor is reconstituted with deionized or distilled water. The enzyme precursor preparation is stable for at least three months when stored at −20°C. in the frozen state or when stored at room temperature in the freeze dried state.

The binding material can be prepared from the enzyme preparation. The enzyme preparation is mixed with an inert osmotic solution and centrifuging in a manner that achieves the separation obtained by a 5 minute centrifugation of a 0.3 M sucrose mixture of the enzyme preparation at about 220 × g (at tip). The liquid suspension is separated and washed free of reagent from the prior steps by conventional means, such as dialysis and centrifugation to yield the binding material. The binding material is stored by freezing at −10°C. or freeze drying.

The binding enzyme exhibit Na-K-ATPase like activity and bind cardiac glycosides; however, they will not bind non-active cardiac glycosides. At the present time I do not know their molecular weight, structure, amino acid sequence or atomic formula, and it appears that due to the largeness and complexity it will be many years before I can more fully elucidate their character. The binding enzyme prepared from the binding enzyme precursor exhibits greater cardiac glycoside binding than the binding enzyme prepared from the binding material and is the preferred enzyme for the present assay.

EXAMPLE 1

Digoxin is extracted from patient serum or from plasma as follows: 5ml of serum or plasma is shaken for 30 seconds with 30ml of Chloroform in a 40ml glass-stoppered conical centrifuge tube, and centrifuged for 2 minutes at 1800 rpm (750 × g at tip). The milky top layer and fatty plug are removed with a teflon-tipped aspirator. The bottom chloroform layer is decanted into another 40ml centrifuge tube and evaporated to dryness in 3 to 5 minutes on a Buchler Evapomixer at 60°C. under vacuum. The digoxin thus extracted is rinsed down to the bottom of the tube with 1ml of ethyl ether and evaporated to dryness in a 50°C. water bath under a stream of filtered air.

One hundred thirty microliters of 100 mM tris-HCl pH 8.0 and 20$\mu$l of toluene are then added. The sample is mixed on a Vari-whirl vortex mixer for 20 seconds at full speed and centrifuged for 3 minutes at 1800 rpm. The top toluene layer is removed with a narrow, drawn-out pasteur pipet, and discarded. Duplicate 50$\mu$l tris aliquots of the bottom tris layer are then assayed in the same manner as for the standards described in Example 3. No quench correction is required. Only raw 1 or 2 minute counts need be used and the counts of duplicate aliquots are averaged. The amount of digoxin found in each aliquot is obtained by comparison with that day's standard curve. These results are then corrected for recovery of glycoside and for the fact that only 50$\mu$l of the 130$\mu$l of the bottom tris layer was taken for each assay.

A complete assay, including assay of standards and scintillation counting of standards plus the serum sample, can easily be done with results available to the physician in less than 2 hours. On the other hand, one technician can process 20 serum samples per working day, with results available that afternoon.

In the above assay, the binding enzyme binds tritiated ouabain in the presence of Na and Mg. The digoxin present in an extract of serum is allowed to compete with a standard amount of $H^3$ ouabain for the enzymatically produced binding sites, thus displacing $H^3$ ouabain from the enzyme. After centrifugation, the unbound $H^3$ ouabain in the supernatant fraction is counted by liquid scintillation and compared with known counts for standard concentrations of digoxin. An increase in supernatant radioactivity indicates uptake of digoxin or other cardiac glycoside at the expense of tritiated ouabain. When ATP is absent, no $H^3$ ouabain or active cardiac glycoside is taken up. Addition of 5mM potassium also reduces uptake of $H^3$ ouabain.

Counting of tritium was done on liquid scintillation counters with tritium efficiency of either 20 or 36%, and employed polyethylene scintillation vials and 10ml of scintillant, which consisted of 21.5 gm 2, 5 -diphenyloxazole, and 375 gm naphthalene dissolved in 3 liters of paradioxane.

The above assay is easy for a laboratory to set up and run. It is also rapid, requiring 2 hours for assay of a single sample. On the other hand, one technician can assay 20 serum samples in one working day, with results ready that afternoon.

EXAMPLE 2

Two ml of animal serum are mixed for about 30 seconds with 8 ml. of methylene chloride. The mixture is centrifuged to break the layers into two distinct fractions; the top layer and fatty plug are removed, and the remainder is evaporated under a stream of dry air or nitrogen at a temperature of between 50° and 80°C. The evaporated residue is taken up in 50 microliters of 100mM tris-HCl having a pH of about 8. Ten microliters of toluene is added and the resulting mixture is thoroughly mixed and centrifuged to separate the layers. The toluene layer is removed and thrown away and the tris buffer layer is divided into two 20 microliter fractions. Each of the tris buffer fractions are placed in a small plastic centrifuge tube containing 10 microliters of the freeze-dried binding enzyme precursor. Ten microliters of a solution containing 30 mM disodium adenosine triphosphate, 30 mM of magnesium chloride, 30 mM of EGTA, 600 mM of sodium chloride and 100 mM of tris-HCl having a pH of about 8 are added to the enzyme serum extraction mixture. This composite solution also contains 0.04 micro Ci tritiated ouabain (Specific Activity 11.7 Ci per millimole). In other identical tubes containing the same amount of freeze-dried binding enzyme precursor and reaction solution are placed gravimetric standards of digoxin. The tubes are incubated for 10 minutes at about 55°C. The enzyme is then separated from the supernatant by centrifuging in a clinical benchtop centrifuge. Twenty microliters of the supernatant is counted on a liquid scintillation counter, a standard curve is constructed from the known samples and the unknown samples are read against the curve in order to determine the concentration of digoxin in the serum sample. This assay procedure requires less than 30 minutes for a single sample.

This assay may also be used to check other cardiac glycosides in an animal serum.

EXAMPLE 3

Figure 3:
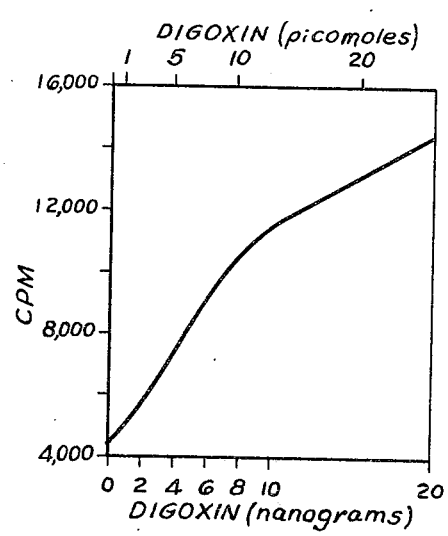
FIG. 3 is a standard graph plotting digoxin concentration v. counts per minute of isotope displaced from the binding enzyme to the supernatant after reaction in the displacement step.

A solution of 250,000 Ng (nanograms) of digoxin per ml of methanol is gravimetrically prepared. This is then serially diluted to yield 20, 10, 5, and 2.5Ng of digoxin per 50ul of 100 mM tris-HCl pH 8.0. To assay the standards, 50ul of binding enzyme precursor, and 20ul of an isotope solution are incubated for 60 minutes at 37°C. The isotope solution contains 22.5 mM disodium adenosine triphosphate, 22.5 mM $MgCl_2$, 22.5mM ethylenebis (oxyethylenenitrilo) -tetraacetic acid (EGTA Eastman No. 8276), 450 mM NaCl, 0.04$\mu$Ci $H^3$ ouabain (Sp. Act. 11.3Ci/mMole) and 100 mM tris. The pH of this solution is between 7.9 and 8.0. Incubation is stopped by centrifugation for 2 minutes in the Beckman micro centrifuge. 50ul of each supernatant is then counted by liquid scintillation. Such a standard curve is run in duplicate, as shown in FIG. 3. It is highly reproducible from day to day.

EXAMPLE 4

Digitoxin, digoxin, and ouabain were dissolved in methanol to equal 250,000 Ng/ml by gravimetric measurement. One 0.1mg pill of digitalis leaf (Burroughs-Wellcome and Co., Lot No. J604) was dissolved in 10ml of methanol. Serial dilutions were then made in 100 mM tris-HCl pH 8.0 equal to 0, 2.5, 5, 10, and 20Ng (or ug of digitalis leaf) per 50$\mu$l respectively. Fifty microliter aliquots of each drug were then incubated and assayed as previously described. As shown in FIG. 4, all four drugs displaced $H^3$ ouabain from the enzyme with approximately equal potency. One microgram of digitalis leaf had approximately equal activity to 1Ng of the pure glycosides, in agreement with common clinical experience.

Recovery of digitoxin by this assay method is about 46 percent, a workable figure. Because digitoxin is less polar than digoxin, more digitoxin appears to be lost into the toluene layer than is digoxin, and less is thus recovered in the 130$\mu$l of tris from which the 50$\mu$l aliquots are taken for assay. The present assay responds well to the presence of digitoxin in the serum of patients.

Example 5

It requires less than 1 working day to prepare enough binding enzyme precursor for about 1000 assays. Three male guinea pigs (9–12 months old) are killed by a blow to the head, and decapitated. The skull is opened and the brain tissue is scraped out and washed and blotted free of blood with distilled water.

Three such brains usually weigh about 13 grams. The tissue is gently homogenized in 20 ml of 0.25M sucrose for 1 minute at 0°C in a teflon and glass homogenizer and transferred to a 40ml conical centrifuge tube. The homogenizer is rinsed with 5ml of 0.25M sucrose, and the combined sample then centrifuged at 4°C for 20 minutes at 3400 rpm (2600 × g at tip of the No. 233 head).

The supernatant is discarded. The pellet is again transferred to the teflon pestle homogenizer. Fifteen ml of 5mM tris-HCl about pH 7.2 is added and the sample homogenized for 1 minute at 0°C. The homogenate is transferred to the centrifuge tube along with a rinse of the homogenizer using 5ml of 5mM tris-HCl pH 7.2. It is again centrifuged at 2600 × g for 20 minutes. The supernatant is again discarded. This procedure is repeated three times for a total of four washes with 5mM tris-HCl pH 7.2

The pellet is then taken up to a volume of 50ml with 5mM tris-HCl pH 7.2. To this is added 50 ml of a solution containing 10mM $CaCl_2$ and 5mM tris-HCl pH 7.2. This homogenate is gently mixed, incubated for 1 hour at 30°C, and then centrifuged at 4°C for 20 minutes at 2600 × g.

The supernatant is discarded. The pellet is taken up with 50 ml of 0.6M sucrose. The volume is then adjusted to 100 ml with water, to give a final concentration of 0.3M sucrose. The sample is then centrifuged at 4°C for 5 minutes at 220 × g at the tip. The milky supernatant is then taken and dialyzed overnight against 2 liters of 5mM tris-HCl pH 8.0 at 4°C, in dialysis tubing.

The dialyzed homogenate is then concentrated by centrigugation at 3400 rpm for 20 minutes to a volume of about 50ml, rehomogenized, and then quick frozen in 1 ml portions in individual 5ml test tubes cooled in a dry ice-acetone bath. This binding enzyme precursor has been successfully prepared 25 times out of 25 efforts to date. It is stable for over three months when stored at −20°C. Alternatively the binding enzyme precursor can be freezedried and stored at room temperature.

EXAMPLE 6

Duplicate reagent blanks are always run each day as controls. They consist of 5ml of 0.10M NaCl instead of serum, and they are processed exactly as the serum samples. One hundred thirty-five reagent blanks had a mean apparent cardiac glycoside level of 0.17 ± 0.17 Ng/ml (1 S.D.).

Serum digoxin has been measured on 76 patients not receiving any type of digitalis. These patients were also receiving at least 45 other drugs, including steroids and common cardiac drugs. The mean apparent cardiac glycoside level for these 76 "patient blanks" was 0.17Ng/ml ± 0.17Ng/ml (1 S.D.), exactly the same as for reagent blanks.

In a further test of specificity, one pill or liquid specimen of each drug found in the medicine cabinet of the Clinical Research Center of the Los Angeles County-University of Southern California Medical Center (130 separate drugs) was taken, and was subjected to assay for Cardiac glycosides. None of the drugs appeared to interfere with the assay.

EXAMPLE 7

Serum digoxin levels were measured in 83 nontoxic patients on the medical wards of the Los Angeles County-University of Southern California Medical Center. Serum was drawn at least 6 hours after the last dose had been given. These patients were free of arrhythmias, nausea, vomiting, visual symptoms, or other adverse manifestations of digoxin therapy. The mean serum digoxin level in this group of patients was 1.43 ± 0.76 Mg/ml (1 S.D.). These results are in close agreement with these found with the immunoassay.

Twenty one patients exhibited various arrhythmias while on digoxin therapy. Serum from these patients was drawn at least 6 hours after the last dose. An average serum level of 3.10 ± 0.76 Ng/ml (1 S.D.) was found, a significantly higher level than that for the nontoxic patients (P <.001). This value agrees closely with the results of the immunoassay, where the average toxic level was 3.3 ± 1.5Ng/ml (1).

Serial determinations of serum digoxin have provided a highly useful means to monitor and to adjust digoxin therapy, especially when a patient's renal function is changing rapidly.

EXAMPLE 8

A 47 year old woman was admitted to this center 3 hours after having ingested 100 tablets of 0.1mg of digitoxin. She had vomited once. Physical examination was unrevealing. An electrocardiogram revealed a sinus mechanism with a rate of 52/min. The P-R interval was 0.24 seconds. Serum was obtained for assay, urine collection was begun, and vigorous gastric lavage was instituted.

Apparent serum digitoxin on admission was 51.0 Ng/ml, a value close to that of another patient whose atrial fibrillation was under satisfactory control on digitoxin 0.1mg/day. In addition, assay of an aliquot of 4 liters of material obtained by gastric lavage revealed cardiac glycosides equivalent to 1.2 $\mu$g/ml of digitoxin, suggesting that the lavage may well have removed 4.8 of the 10mg that was ingested. The results from both the serum and gastric material were in the hands of ward personnel within 3 hours.

On the basis of this assay information, especially the findings from the gastric material, it was decided by those caring for the patient that she might just have passed the stage where serum levels were highest. Since they were not severe, and since only mild AV block was present, it was felt that she might do well subsequently without further intervention. She was carefully watched, and in fact recovered without further therapy. Subsequent daily serum digitoxin levels were 41, 31.6, and 24.4 Ng/ml, while spot checks of two urine specimens for urinary digitoxin excretion (extracting 0.5 ml of urine for assay) yielded apparent digitoxin concentrations of 848 and 512 Ng/ml on the two days after admission. Four control urine specimens and six specimens at gastric contents from persons not receiving any digitalis gave negative results.

I claim:

1. A binding enzyme precursor for an enzymatic binding radioisotope displacement assay for cardiac glycosides in serum, said binding enzyme precursor produced by the process comprising the following steps: homogenizing animal tissue sensitive to cardiac glycosides in an aqueous osmotic solution to produce a homogenate containing a solid phase and a liquid phase, said tissue having Na-K-ATPase activity; separating the solid phase from the liquid phase; at last once homogenizing said solid phase in an aqueous buffered solution to produce a homogenate containing a solid phase and liquid phase and separating said solid phase from the liquid phase to obtain a binding enzyme preparation; reacting the binding enzyme preparation with calcium in an aqueous buffered solution having a pH of between about 6 and 9 to yield the binding enzyme precursor, at least 0.01 millimole of calcium being used for each gram of tissue used in the preparation.

2. The binding enzyme precursor according to claim 1 wherein the binding enzyme preparation is reacted with between about 0.01 and 0.2 millimole of calcium for each gram of tissue used in the preparation of the binding enzyme precursor.

3. The method according to claim 2 wherein said reaction is conducted at a temperature of about 30°C.

4. The binding enzyme precursor according to claim 1 purified by the following steps after reacting with calcium mixing the reaction product between said enzyme preparation and calcium with an inert osmotic solution to form a solid and a liquid phase; and separating the solid and liquid phase by centrifuging at a force equivalent to a 5 minute centrifugation of a 0.3M sucrose solution at about 220 × g; separating a supernatant and washing it free of the reagents from the prior steps to yield the purified binding enzyme precursor.

5. The binding enzyme precursor as defined in claim 4 wherein said binding enzyme precursor is frozen at a temperature below about −10°C. or is freeze-dried for enhanced storage life.

6. A binding enzyme for the enzymatic binding radioisotope displacement assay for serum cardiac glycosides, said enzyme exhibiting Na-K-ATPase activity, said binding enzyme being the product of the following step: reacting the binding enzyme precursor as set forth in claim 1 with a high energy phosphate compound.

7. The enzyme as defined in claim 6 wherein said precursor and high energy phosphate compound are reacted in the presence of magnesium.

8. The enzyme as defined in claim 6 wherein said precursor and high energy phosphate compound are reacted in the presence of magnesium.

9. The enzyme according to claim 6 wherein the binding enzyme precursor and the high energy phosphate compound are reacted at a temperature between about 25° and 55 20 C. in the presence of between about 2 and 2,000 micromoles of magnesium and between about 40 and 24,000 micromoles of sodium for each equivalent of said precursor.

10. The enzyme according to claim 6 wherein said precursor, for each equivalent thereof, is reacted with between about 4 and 100 micromoles of ATP.

11. The enzyme according to claim 6 wherein said precursor and the high energy phosphate compound are reacted in the presence of between about 2 and 2,000 micromoles of a heavy metal chelating agent for each equivalent of said precursor.

12. A method of preparing a binding enzyme for enzymatic binding radioisotope displacement assays for serum cardiac glycosides, said enzyme exhibiting Na-K-ATPase activity, said method comprising homogenizing an animal tissue having Na-K-ATPase activity in a sugar solution having a molarity of between about 0.1 and 1 to produce a homogenate containing a solid phase and a liquid phase; separating the solid phase from the liquid phase; at least once homogenizing the solid phase in a buffered solution to produce a homogenate containing a solid phase and a liquid phase and separating the solid phase therefrom to yield a binding enzyme preparation, said buffered solution being hypoosmotic; reacting the enzyme preparation, for each gram of tissue used in the preparation, with between 0.01 and 0.2 millimole of calcium at a temperature of about 30°C in a buffered solution to yield a solid phase and a liquid phase and separating the solid phase therefrom to yield the binding enzyme precursor; purifying the binding enzyme precursor by mixing the separated solid phase in an inert osmotic solution having an osmolality of between about 0.1 and 1, separating a supernatant liquid from the mixture by centrifuging in a manner equivalent to that achieved by centrifuging a 0.03M sucrose solution for about 5 minutes at about 220 × g; washing the supernatant free of all reagents from the previous steps to produce a purified binding enzyme precursor; reacting the binding enzyme precursor, for each equivalent thereof, with between about 4 and 100 micromoles of ATP in a buffered solution containing between about 2 and 2,000 micromoles of magnesium, between about 2 and 2,000 micromoles of EGTA, between about 0.04 and 24 millimoles of sodium and with a sufficient amount of a buffering agent to maintain the pH of the reaction mixture at a relatively constant value between about 6 and 9, said reaction being conducted at a temperature of between about 25° and 55°C to yield the binding enzyme.

13. The method according to claim 12 wherein said purified enzyme precursor is reacted with between about 10 and 250 millimoles of ATP.

* * * * *

UNITED STATES PATENT AND TRADEMARK OFFICE
CERTIFICATE OF CORRECTION

PATENT NO. : 3,959,077

DATED : May 25, 1976

INVENTOR(S) : Gray Brooker

Page 1 of 2

It is certified that error appears in the above-identified patent and that said Letters Patent are hereby corrected as shown below:

Column 2, line 55, "radiactive" should be --radioactive--

Column 3, line 6, after "activity" "of" should be --by--

Column 5, line 9, before "its" delete --as--

Column 5, line 39, "preferably" should be --preferable--

Column 6, line 2, "y" should be --yl--

Column 6, line 42, "$\mu$" should be --$\mu$1--

Column 6, line 43, "$\mu$" should be --$\mu$1--

Column 6, line 45, before "is" insert --it--

Column 6, line 57, after "aglycone" "of" should be --or--

Column 8, line 21, "Na-KATPase" should be --Na-K-ATPase--

Column 13, line 67, "at" should be --of--

Column 14, line 53 (Claim 8), "magnesium" should be --sodium--

Column 14, line 57 (Claim 9), "25°and 55 20C." should be --25 and 55°C.--

Column 16, line 7 (Claim 12), before "binding" insert --purified--

UNITED STATES PATENT AND TRADEMARK OFFICE
CERTIFICATE OF CORRECTION

PATENT NO. : 3,959,077
DATED : May 25, 1976
INVENTOR(S) : Gary Brooker

It is certified that error appears in the above-identified patent and that said Letters Patent are hereby corrected as shown below:

Column 16, line 11 (Claim 12), before "EGTA" delete --of--

Column 16, line 19 (Claim 13), before "enzyme" insert --binding--

Signed and Sealed this

Fifth Day of October 1976

[SEAL]

Attest:

RUTH C. MASON
Attesting Officer

C. MARSHALL DANN
Commissioner of Patents and Trademarks